United States Patent [19]

Bakos et al.

[11] Patent Number: 5,132,001
[45] Date of Patent: Jul. 21, 1992

[54] HEMISPHERAND IONOPHORES HAVING INCREASED LIPOPHILICITY

[76] Inventors: Vincent W. Bakos; Daniel S. Daniel; John L. Toner, all of Kodak Park Division, Rochester, N.Y. 14650

[21] Appl. No.: 526,262

[22] Filed: May 21, 1990

[51] Int. Cl.[5] ............................................. G01N 27/26
[52] U.S. Cl. ................................. 204/416; 204/418; 204/420
[58] Field of Search ........................ 204/416, 418, 420

[56] References Cited

U.S. PATENT DOCUMENTS 4,476,007 10/1984 Toner et al. ................ 204/418

Primary Examiner—John Niebling
Assistant Examiner—Bruce F. Bell
Attorney, Agent, or Firm—John R. Everett

[57] ABSTRACT

Sodium ion selective compositions which comprise an ion carrier, a compound capable of solvating the ion carrier, and a supporting matrix are disclosed.

The ion carriers of this invention are hemispherand compounds represented by the formula

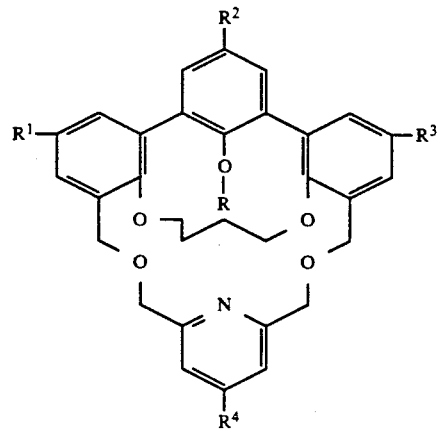

wherein $R^1$, $R^2$, $R^3$, and $R^4$ are independently hydrogen, alkyl, alkenyl, cycloalkyl, aryl or a heterocyclic group and R represents Z-decyl, Z-octyl, 3-octyl, and cyclohexyl methyl.

14 Claims, No Drawings

HEMISPHERAND IONOPHORES HAVING INCREASED LIPOPHILICITY

FIELD OF THE INVENTION

This invention relates to hemispherand compounds and to their use in ion selective compositions and ion-selective electrodes.

DESCRIPTION RELATIVE TO THE PRIOR ART

In the diagnosis and treatment of various diseases as well as in preventative health checkups, it is becoming increasingly important to monitor the concentrations of certain ions in a patient's body. Cations which have merited considerable attention in the diagnosis and treatment of heart disease, manic depressive psychosis, kidney disease, diabetes and hypertension are alkali metal ions, e.g. lithium, sodium and potassium.

One type of ion-selective electrode has an electrode body (usually a glass container) containing a reference solution in contact with a half-cell of known potential (a reference electrode) and an ion-selective glass membrane located in an aperture in the electrode body. The ion-selective membrane is mounted in such a fashion that, when the electrode is immersed in the unknown solution, the membrane contacts both the reference and unknown solutions. A metal probe coated with a layer of insoluble salt of the metal in the reference solution and immersed therein serves as one of the contacts for measuring the potential between the electrodes and provides a reference potential for the electrode. The sensitivity of the electrode to an ion in solution is determined by the composition of the glass membrane. This type of electrode is referred to in the art as a "barrel" electrode.

In addition to the glass membranes, polymeric ion-sensitive membranes are also known. These membranes generally comprise a polymeric binder or support as the supporting matrix which is impregnated with a solution of an ion-sensitive carrier in a carrier solvent. The ion-sensitive carrier is a compound which is capable of sequentially complexing the desired ion, transporting the ion through the membrane and releasing the ion. This compound is also referred to in the art as an "ionophore" or "ion carrier". Depending upon the ionophore, solvent and binder, membranes of this type can be used to detect a particular ion preferentially to other ions which may be in the solution.

U.S. Pat. No. 4,476,007 describes a generic class of hemispherands useful as ionophores in ion-selective compositions, membranes and electrodes. The hemispherands disclosed therein have the structure:

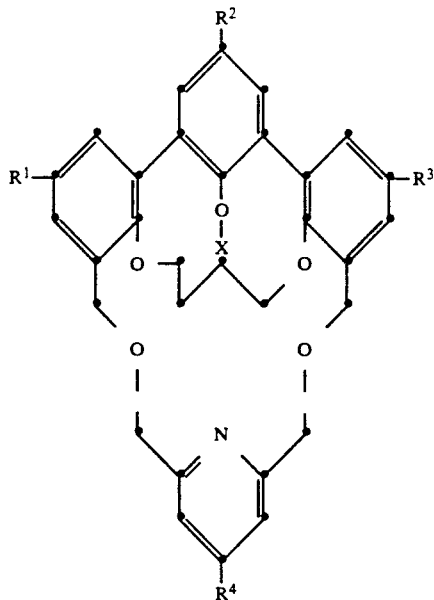

wherein $R^1$, $R^2$, $R^3$ and $R^4$ are independently hydrogen, alkyl, alkenyl, cycloalkyl, aryl or a heterocyclic group; and X is benzyl or an electron donating group capable of forming at least one coordinating site for sodium ions.

The disclosed hemispherands provided a high degree of selectivity of sodium ions over potassium ions in assays of biological fluids. The problem is that the particular hemispherands actually disclosed do not provide ion-selective compositions and ion-selective electrodes having a higher degree of precision in sodium assays.

SUMMARY OF THE INVENTION

The present invention provides a sodium ion-selective composition comprising a solvating compound and a hemispherand represented by the structure:

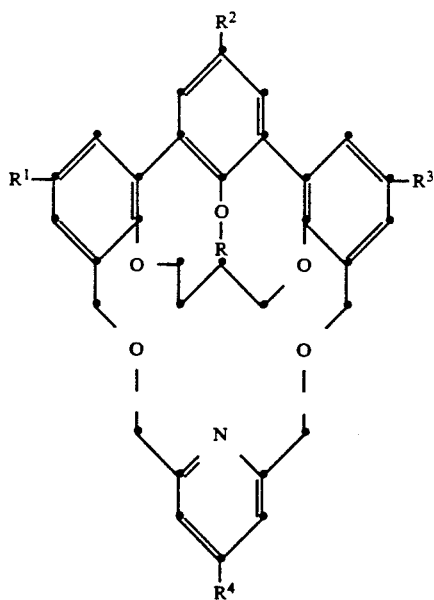

wherein $R^1$, $R^2$, $R^3$ and $R^4$ are independently hydrogen; or a group selected from alkyl (substituted or unsubstituted), preferably of from 1 to 12 carbon atoms (e.g.

methyl, ethyl, isopropyl, t-butyl, hexyl, etc.), alkenyl (substituted or unsubstituted), preferably of from 2 to 12 carbon atoms (e.g. allyl, vinyl, 1-propenyl, etc.) cycloalkyl (substituted or unsubstituted), preferably of from 3 to 10 carbon atoms (e.g. cyclopropyl, cyclohexyl, etc.), aryl (substituted or unsubstituted), preferably of from 6 to 12 carbon atoms (e.g. phenyl, tolyl, xylyl, methoxyphenyl, etc.), and heterocyclic groups (substituted or unsubstituted), preferably of 5 to 10 nuclear atoms (e.g. pyridyl, etc.). Any of these R groups can be substituted with one or more halo, nitro, amino, alkoxy or other suitable groups as known by one skilled in the art. Preferably, each of $R^1$, $R^2$, $R^3$ and $R^4$ is hydrogen or alkyl (e.g. of 1 to 6 carbon atoms). More preferably, two or more of $R^1$, $R^2$, $R^3$ and $R^4$ are the same alkyl, e.g. methyl.

R represents an oleophilic group having 8 to 22 carbon atoms.

The present invention also provides novel hemispherands having the structure:

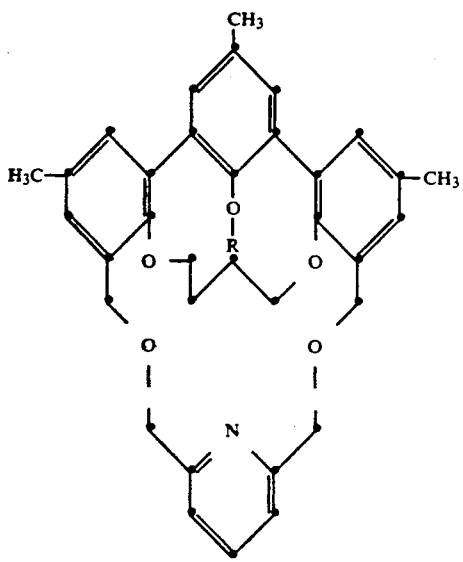

wherein R represents 2-decyl, 4-t-butylbenzyl, 2-octyl; 3-octyl and cyclohexylmethyl.

These compounds are useful as ionophores in ion-selective compositions and electrodes. They are more lipophilic than the expressly disclosed compounds of U.S. Pat. No. 4,476,007, have equivalent selectivity for sodium ion over potassium ion and provide unexpectedly better precision in sodium assays.

This invention also provides a composition comprising a hemispherand of this invention, a compound capable of solvating it and a supporting matrix. This composition is useful as an-ion selective membrane. In preferred embodiments, the solvating compound is a hydrophobic carrier solvent and the supporting matrix is a hydrophobic binder.

There is also provided an ion-selective electrode having an ion-selective membrane composition comprising as an ionophore a hemispherand of this invention, a compound capable of solvating the hemispherand, and a supporting matrix.

There is also provided a dry operative ion-selective electrode comprising a hemispherand ionophore of this invention dissolved in a compound capable of solvating the hemispherand.

DETAILED DESCRIPTION OF THE INVENTION

Generically, hemispherands and related compounds are compounds which were first developed by Dr. D. J. Cram and his coworkers (see Journal of the American Chemical Society, 101:22, October, 1979, and 101:13, June, 1979, J. C. S. Chem. Comm., page 948, 1979).

A hemispherand is a macrocylic compound wherein at least a portion of the macrocyclic ring contains contiguous rigid cyclic units, at least some of these units having coordinating sites for ions. The rigid cyclic units are sufficient in number to rigidize a portion of the macrocyclic ring structure. The coordinating sites in the cyclic units are oriented so as to face the interior of the macrocycle, thereby forming the rigidized portion of the macrocyclic cavity in the molecule for receiving ions.

Lipophilic hemispherands are hemispherands which contain no solubilizing groups such as carboxylic acid groups or sulfonic acid groups, or which contain sufficiently large oil-soluble groups to render the molecule oil-soluble, e.g., capable of forming a 4%-by-weight solution of the hemispherand in a hydrophobic organic solvent.

In addition to the lipophilic hemispherand, the compositions of the present invention include a compound which is capable of solvating the hemispherand. Solvation is necessary so that sodium ions are transported through the membrane by the solvating hemispherand. In some embodiments, one or more polymeric binders which are capable of solvating the hemispherand are used. If the polymer is capable of dissolving, at least partially, the hemispherand, it is useful in this embodiment. Exemplary polymers which are so useful are described in U.S. Pat. No. 3,419,634. The preparation of ion-selective membranes using these solvating polymers is described in U.S. Pat. No. 3,743,588. In these embodiments, the polymer functions as both the compound which is capable of solvating the hemispherand and the supporting matrix for the composition.

In other and preferred embodiments, the hemispherand is solvated by one or more separate organic solvents and the supporting matrix is a separate component. Such a matrix must allow for the transport of the sodium ions which are bound to the hemispherand in the organic solvent. For example, a porous glass support is useful as the supporting matrix. In these embodiments, the hemispherand is dissolved in the organic solvent and then the resulting solution is imbibed into the porous glass support to provide an ion-selective membrane. In other embodiments, the solution of the hemispherand is dispersed in a hydrophobic binder. By "hydrophobic" is meant substantially water-insoluble. The binder dispersion is coated and dried to produce an ion-selective membrane according to the present invention.

Where a separate solvent is used to solvate the hemispherand, the solvent can be any of a wide variety of solvents, provided that it is capable of at least partially dissolving the hemispherand. The solvent, sometimes referred to in the art as a carrier solvent, provides sodium ion mobility in the membrane. If a hydrophobic binder is used as the supporting matrix, the solvent must be compatible with the binder.

Useful carrier solvents are hydrophobic organic solvents including phthalates, sebacates, aromatic and aliphatic ethers, phosphates, mixed aromatic aliphatic phosphonates, adipates, nitrated ethers or esters and mixtures of these solvents. Particularly useful solvents include dibutyl sebacate, bromophenyl phenyl ether, bis(2-ethylhexyl) 4-nitrophthalate, o-nitrophenyl valerate, dioctyl phenylphosphonate, o-nitrophenyl phenyl ether, o-nitrophenyl octyl ether, triisodecyl trimellitate, dimethyl phthalate, diisodecyl phthalate and tris(2-ethylhexyl) phosphate. Diisodecyl phthalate is a particularly preferred solvent when a 2'-oleophilic group-substituted-3,3'''-[2,6-pyridylenebis(methyleneoxymethylene)]2,2'''-tetramethylenedioxy-5,5',5''-trimethyl-1,1':3',1''-terphenyl is used as the ionophore in the sodium-selective compositions and electrodes of this invention.

If the hemispherand is included in a carrier solvent as described above, a membrane is formed using a dispersion of the solvent-hemispherand in one or more binders as the supporting matrix. Useful binders include hydrophobic natural or synthetic polymers capable of forming thin films of sufficient permeability to produce, in combination with the hemispherands and carrier solvent, ionic mobility across the membrane. Useful polymers include (poly(vinyl chloride); poly(vinylidene chloride); poly(acrylonitrile); polyurethanes, particularly aromatic polyurethanes; copolymers of vinyl chloride and vinylidene chloride; poly(vinyl butyral); poly(vinyl formal); poly(vinyl acetate); silicone elastomers; and copolymers of vinyl alcohol, cellulose esters and polycarbonates. Other useful polymers include carboxylated polymers of poly(vinyl chloride) and mixtures and copolymers of these materials. Membranes including binders, the hemispherands and carrier solvents are prepared using conventional film-coating or casting techniques.

The membranes of the present invention contain the described components over a wide range of concentrations or coverages. The coverage of the hemispherand depends upon the compound used to solvate it, as well as other factors. The preferred membranes comprise a hydrophobic binder having the solvent and hemispherand dispersed therein. In these membranes, hemispherand coverages of between about 0.1 g/m$^2$ and 2.0 g/m$^2$ are useful and coverages between 0.2 g/m$^2$ and 0.8 g/m$^2$ are preferred.

The carrier solvent is present in an amount sufficient to solvate the hemispherand. The amount therefore depends on the particular solvent and hemispherand chosen. Generally, more solvent is used than is necessary to solvate the hemispherand so that it remains solvated under a variety of storage conditions. A 100 percent or 500 percent excess on a weight basis is useful. Usually, the coverage of carrier solvent will be within the range of about 2 g/m$^2$ to 24 g/m$^2$.

The amount of hydrophobic binder which is present is determined by the desired thickness of the membrane and by the necessity for providing support for the hemispherand-solvent dispersion. The membranes generally have a thickness in the range of from about 2 $\mu$m to about 20 $\mu$m. The binder coverage is usually between about 2 and 24, and preferably from about 3 to about 12 g/m$^2$.

In addition to the binder, hemispherand and solvent, the membranes of the present invention optionally contain other components such as surfactants and plasticizers in amounts known to those skilled in the art.

Surfactants are useful components of the described membranes. The surfactants serve a variety of functions including improving the coatability of the membrane composition and improving the solvation of the hemispherand by the binder or solvent. Useful surfactants include nonionic surfactants such as the alkylaryl polyether alcohols (Tritons TM) available from Rohm and Haas Co.; (p-isononylphenoxy)polyglycidol (Surfactant 10G TM) available from Olin Mathieson Corp.; polyoxyethylene (20) oleyl ether (Brij 98 TM), polyoxyethylene sorbitan monolaurate (Tween 20 TM) and Span 80 TM, all available from Atlas Chemical Industries; poly(dimethyl-co-methylphenyl siloxane) (DC-510 TM) available from Dow Corning; Zonyl FSN TM available from E.I. duPont; and fluorochemical surfactant FC134 TM available from 3M Co.

A useful ion-selective electrode comprises:
(a) a reference electrode in contact with
(b) a reference composition which is, in turn, in contact with one side of
(c) an ion-selective membrane of the type described hereinabove.

In one embodiment, the ion-selective electrode is in the form of a glass tube. The ion-selective membrane forms the bottom of the tube. The tube is at least partially filled with a salt solution of known concentration forming the reference composition. Immersed in the reference composition is a reference electrode which is a metal electrode having a thin metal salt layer on its outer surface. The ion-selective electrode is used by immersing at least the membrane of the electrode in the unknown solution. One side of a voltmeter is connected to the reference electrode immersed in the reference composition and the other side is connected to a conducting probe in the unknown solution. The potential which develops across the voltmeter is proportional to the difference in ion concentration between the unknown solution and the reference composition.

The membranes of the present invention are useful in a variety of electrode structures. For example, the membranes of the present invention are useful in place of, or in addition to, the glass ion-selective membrane of a conventional barrel-type electrode. Useful electrodes of this type are disclosed, for example in U.S. Pat. Nos. 3,598,713, 3,502,560, 3,562,129, 3,691,047, 3,753,887, 3,833,495, 3,671,414 and 3,743,588. The membranes are also useful in the ion-selective electrodes described in Japanese Patent Publication Nos. 17851/1982 and 17852/1982, both published Jan. 29, 1982, and particularly in the dry ion-selective electrodes described therein.

In particularly preferred embodiments, the hemispherand-containing membrane of the present invention is used in a dry-operative ion-selective electrode as described in U.S. Pat. No. 4,214,968 noted hereinabove. In this embodiment, there is provided a dry-operative ion-selective electrode comprising:
(a) a dried internal reference element comprising the dried residue of a solution of a salt and a hydrophilic polymeric binder in a solvent for the polymer and the salt and,
(b) in contact with the reference element, a hydrophobic ion-selective membrane of predetermined uniform thickness in regions thereof intended for contact with the sample for analysis, the membrane comprising a hydrophobic binder having distributed therein the lipophilic hemispherand ion carrier described hereinabove dissolved in a carrier solvent.

In this embodiment of the present invention, the electrodes are made by a process using components which are described in U.S. Pat. No. 4,214,968, supra, the disclosure of which is hereby incorporated by reference in its entirety. As used throughout this specification and in the claims, the expressions "dry-operative", "dried" and "uniform" have the meanings defined in U.S. Pat. No. 4,214,968.

The membranes and electrodes of this invention can be used to determine the concentration of sodium in an aqueous solution, e.g. biological fluids such as blood sera and urine. It is particularly useful in determining sodium ion concentration in urine having a high potassium ion concentration. Generally, a portion of the solution to be assayed is brought into contact with the electrode (e.g. a dry ion-selective electrode) described hereinabove which is capable of making potentiometric measurements related to the sodium ion concentration. Subsequently, the difference in potential between the portion of aqueous solution and the reference electrode is measured. Preferably, a drop of the aqueous solution is spotted onto the ion-sensitive membrane of such electrode, but other ways of contacting the electrode with the solution are acceptable.

The following examples are presented to illustrate the practice of this invention.

The following examples 1–6 illustrate a procedure for making the hemispherands of this invention.

EXAMPLE 1

Preparation 1

Preparation of the intermediate 2'-Hydroxy-3,3''-(2,6-pyridylene-bis(methyleneoxymethylene))-2,2''-tetramethylenedioxy-5,5',5''-trimethyl-1,1':3',1''-terphenyl (HCP)

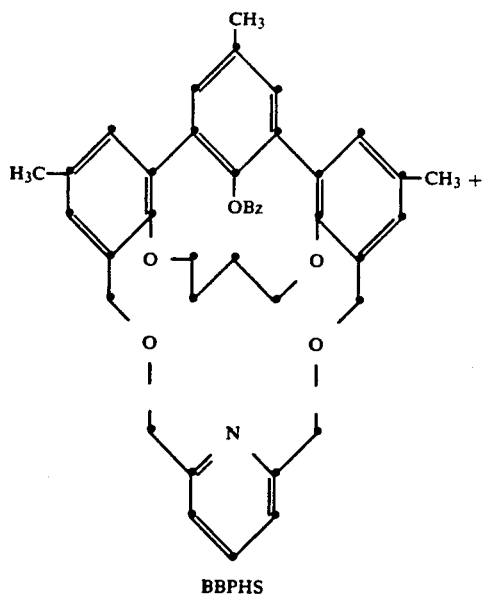

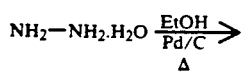

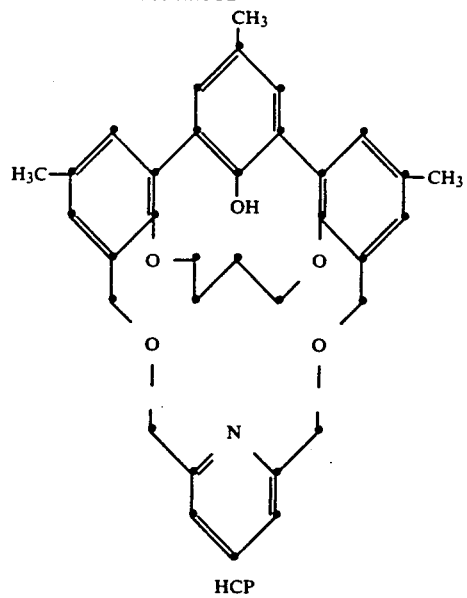

The preparation of the 2'-benzyl compound "BBPHS" is given as Example 1 of US-A-4,476,007. BBPHS (35.2 g, 48.2 mmol) was slurried in 1.2 L abs EtOH and 10% Pd/C (3.6 g, 3.4 mmol Pd), and hydrazine hydrate (36 mL, 740 mmol) was added. The stirred mixture was refluxed for 2 hours, then filtered through diatomaceous earth while still hot. The solid cake was washed thoroughly with $CH_2Cl_2$, and the combined filtrates were stripped. The resulting solid residue was dissolved in $CH_2Cl_2$ and washed with 3 volumes of purified water. The organic phase was separated, dried over $Na_2SO_4$, filtered and stripped to give an off-white solid. Recrystallization from MeCN gave the centerhydroxy product "HCP," 28.6 g (95.0%); FDMS: m/e 537 (M+); Anal. Calc. for $C_{34}H_{35}NO_3 - \frac{1}{2} H_2O$: C, 74.7; H, 6.6; N, 2.6. Found: C, 75.0; H, 6.7; N, 2.4.

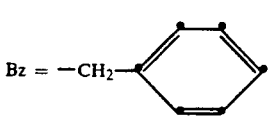

Preparation 2

General Procedure for Alkylation of Hemispherand Center Phenol (HCP)

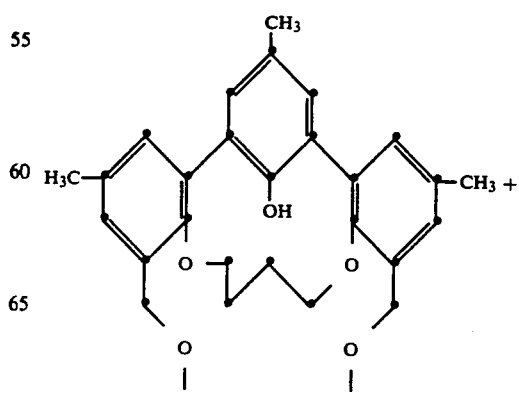

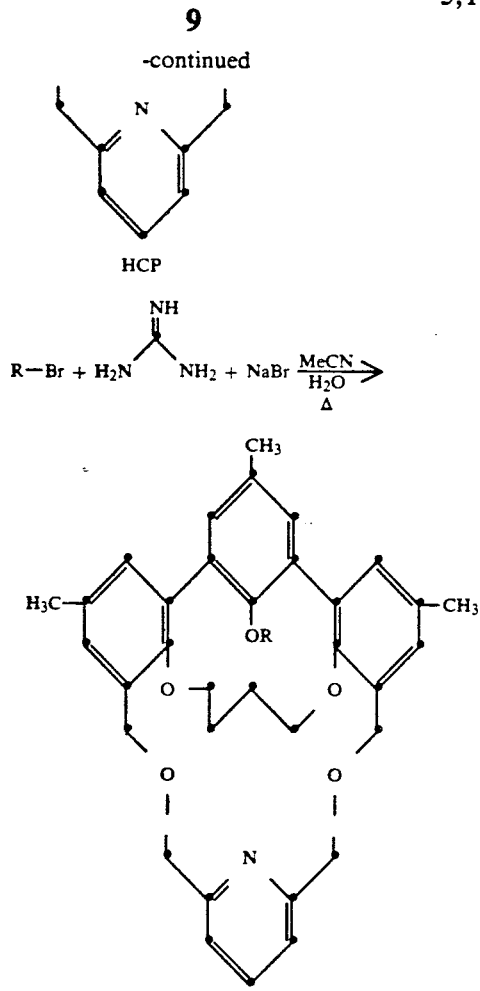

The hemispherand center phenol (HCP) and 1.04 equivalent of NaBr were suspended in MeCN (250 mL/g HCP) and 1.25-2.0 equivalent of 1,1,3,3-tetramethylguanidine (TMG) was added. The mixture was refluxed until the HCP dissolved then purified $H_2O$ (20 mL/g HCP) was added to give a homogeneous solution. The alkyl bromide (1.25-2.0 equivalent) was added and the mixture refluxed. The progress of the reaction was monitored by TLC on $SiO_2$ with 8% $MeOH/CH_2Cl_2$ eluant. Excess TMG and alkylating agent were periodically added to equimolar amounts, usually in 0.25 or 0.50 equivalent increments up to a maximum of 3.0 equivalents, until TLC showed the reaction to be complete or until no further reaction occurred. The total reaction time was 6-13 days.

The reaction mixture was stripped on the rotary evaporator, and the foamy residue was dissolved in $CH_2Cl_2$. After washing 3 times with purified $H_2O$, the organic phase was shaken for 1 minute with saturated aqueous NaBr to form the alkylated hemispherand sodium bromide complex. The $CH_2Cl_2$ layer was dried over $Na_2SO_4$, filtered, and stripped to give a foamy solid residue. Ether was added, and the foam was dissolved with the aid of sonication. Continued sonication after dissolution crystallized the NaBr-complexed product. After storage in the freezer overnight, it was filtered and washed with cold $Et_2O$.

Shaking a $CH_2Cl_2$ solution of the complexed material with 3 volumes of purified water and workup as before gave the uncomplexed chelator as a white foamy solid. In most cases, the foam could be crystallized by sonication with an appropriate solvent, e.g., MeCN. The overall yield of uncomplexed hemispherand was 40-90%, based on HCP (see Table I). The NMR and IR spectra were consistent with the desired structures in all instances.

EXAMPLE 2

3-2'-(-Octyloxy)-3,3''-(2,6-pyridylenebis(methyleneoxymethylene))-2,2''-tetramethylenedioxy-5,5',5''-trimethyl-1,1':3',1''-terphenyl Reaction of HCP (8.00 g, 14.9 mmol) and NaBr with a total of 1.6 equivalent 1-bromoctane and TMG in $MeCN/H_2$) for 6 days in accordance with the general procedure Preparation 2 gave the center 1-octyloxy hemispherand (5.90 g, 61.0%) as a white foam after workup. Crystallization of a sample from MeCN gave a white solid with mp 136°-138° C. FDMS: m/e 672 $(M+Na)^+$, 650 $(M+H)^+$. Anal. Calc. for $C_{42}H_{51}NO_5$: C, 77.62; H, 7.91; N, 2.16. Found: C, 77.70; H, 7.86; N, 2.17.

EXAMPLE 3

2'-(1-Octadecyloxy)-3,3''-(2,6-pyridylenebis(methyleneoxymethylene))-2,2''-tetramethylenedioxy-5,5',5''-trimethyl-1,1':3',1''-terphenyl HCP (2.00 g, 3.72 mmol) and NaBr were reacted with a total of 2.0 equivalent of 1-bromooctadecane and TMG in acetone/$H_2O$ for 11 days according to the procedures of general Preparation 2. Acetone was used in this case due to the low solubility of the alkylating agent in MeCN. Workup to the NaBr complex and crystallization from EtOAc gave 2.39 g (72.0%) of the complexed center 1-octadecyloxy product. Decomplexation of a 1 g portion of this material, followed by trituration of the crude foam with hot MeCN and cooling in the freezer, afforded 0.60 g of a white waxy solid melting over a wide range above 60° C. FDMS: m/e 812 $(M+Na)^+$, 790 $(M+H)^+$. Anal. Calc. for $C_{52}H_{71}NO_5$: C, 79.05; H, 9.06; N, 1.77. Found: C, 79.02; H, 9.24; N, 1.70.

EXAMPLE 4

2'-(1-methylnonyloxy)-3,3''-(2,6-pyridylenebis(methyleneoxymethylene))-2,2''-tetramethylenedioxy-5,5',5''-trimethyl-1,1':3',1''-terphenyl Refluxing HCP (8.00 g, 14.9 mmol) and NaBr for 6 days with a total of 2.5 equivalent of 2-bromodecane and TMG in $MeCN/H_2O$ followed by workup and crystallization of the NaBr-complex from $Et_2O$ gave 10.22 g solids contaminated with the starting phenol. Three recrystallizations from $Et_2O$ gave the complexed product free from starting material. Decomplexation and workup in the usual way afforded the center alkylated product as a white solid foam, 6.89 g (68.3%). A small sample crystallized from cold $Et_2O$ had a mp 119°-121° C. FDMS: m/e 677 $(M+)$. Anal. Calc. for $C_{44}H_{55}NO_5$: C, 77.96; H, 8.18; N, 2.07. Found: C, 78.16; H, 8.33; N, 2.07.

EXAMPLE 5

2'-(1-Ethylhexyloxy)-3,3''-(2,6-pyridylenebis(methyleneoxymethylene))-2,2''-tetramethylenedioxy-5,5',5''-trimethyl-1,1':3', 1''-terphenyl HCP (3.00 g, 5.58 mmol) and NaBr were refluxed with a total of 3.0 equivalent of 3-bromooctane and TMG in $MeCN/H_2O$ for 11 days. Workup and crystallization of the NaBr-complexed product from Et₂O yielded material with phenol contamination that could not be removed by multiple recrystallizations. The product was decomplexed in the usual way and chromatographed on a column packed with Woelm silica gel with 8% McOH/CH₂Cl₂ eluant to remove unreacted starting material. The uncomplexed hemispherand left at the head of the column was complexed in situ by flushing with 500 mL $10^{-2}$M NaI in 8% MeOH/CH₂Cl₂ and eluated with 8% NaOH/CH₂Cl₂. The foamy residue left after stripping was dissolved in CH₂Cl₂, shaken with aqueous Na₂S₂O₃, and decomplexed in the normal manner. Workup and recrystallization from MeCN gave the uncomplexed center 1-ethylhexyloxy hemispherand (1.62 g, 44.6%) as a white microcrystalline powder, mp 126°–129° C. FDMS: m/e 649 (M+). Anal. Calc. for $C_{42}H_{51}NO_5$: C, 77.62; H, 7.91; N, 2.16. Found: C, 77.44; H, 7.81; N, 2.08.

EXAMPLE 6

2'-(Cyclohexylmethoxy)-3,3''-(2,6-pyridylenebis(methyleneoxymethylene))-2,2''-tetramethylenedioxy-5,5',5''-trimethyl-1,1'',3',1''-terphenyl Reaction of HCP (5.00 g, 9.30 mmol) and NaBr with a total of 2.5 equivalent of cyclohexylmethyl bromide and TMG in refluxing MeCN/H₂O for 10 days followed by the usual workup and two recrystallizations from CH₂Cl₂/MeCN afforded the uncomplexed center cyclohexylmethoxy hemispherand (5.11 g, 86.8%) as a crystalline solid, mp 211.5°–214° C. FDMS: m/e 633 (M+). Anal. Calc. for $C_{41}H_{47}NO_5$: C, 77.69; H, 7.47; N, 2.21. Found: C, 77.74; H, 7.52; N, 2.15.

TABLE I

Alkylation Hemispherand Center Phenol (Hemi-OH + R—Br + TMG + NaBr ⟶ Hemi-OR)

| R | g HCP | Eq R—Br & TMG Initial | Eq R—Br & TMG Final | Reaction Time (Days) | Yield |
|---|---|---|---|---|---|
| 1-Octyl | 8.00 | 1.5 | 1.6 | 6 | 61 |
| 1-Octadecyl | 2.00 | 1.25 | 2.0 | 11 | 72 |
| 1-Methylnonyl | 8.00 | 1.5 | 2.5 | 6 | 68 |
| 1-Methylheptyl | 3.00 | 2.0 | 3.0 | 10 | 76 |
| 1-Ethylhexyl | 3.00 | 2.0 | 3.0 | 13 | 45 |
| —CH₂—⟨S⟩ | 5.00 | 2.0 | 2.5 | 10 | 87 |

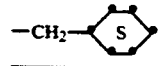

EXAMPLE 7

Evaluation of the Precision and Selectivity of the Hemispherands of this Invention The compounds of this invention were incorporated into ion-selective electrodes (ISEs) constructed in a slide format as described in D. P. Hamblen et al U.S. Pat. No. 4,171,246 issued Oct. 16, 1979 to allow testing experiments to be performed with an Ektachem 700 analyzer. The electrodes used in this example were prepared by the methods described in C. J. Battaglia et al U.S. Pat. No. 4,214,968 issued Jul. 29, 1980.

Each electrode comprised a polyester support having layers in sequence as follows: a silver/silver chloride reference electrode; an electrolyte layer comprising 5 g/m² of gelatin, 2.5 g/m² of NaCl, 0.37 g/m² of glycerol, and 0.06 g/m² of a surface active agent, Olin Surfactant 10G ™ and a membrane layer comprising 10.0 g/m² of a 1.8% carboxylated poly(vinyl chloride) binder, 12 g/m² of bis(2-ethylhexyl) sebacate (BEHS) as a carrier solvent, and 0.06 g/m² of DC-510 ™, a poly(-dimethyl-co-methylphenyl siloxane) surfactant available from Dow Corning.

To study the precision of the resulting elements, a large coating of an electrode was cut to form individual elements which were formatted as slides and the slides were loaded into 1 to 20 Ektachem cartridges. Therefore, each cartridge contained ISEs cut from a position further along the large coating so that the test samples in different cartridges were from different locations of the original coating. Tests were then run on an Ektachem 700 analyzer using slides from at least one of the 1st, 5th, 10th, 15th and 20th cartridges. The tests were performed on 20 slides from each cartridge to determine the mean deviations and calculate the "coefficient of variance" (% CV). The analyzer was calibrated for the slides with fluid standards, and each slide was used to determine the amount of Na+ in human serum by spotting each slide on one side with a solution of known Na+ concentration, and on the other side with the human serum, and analyzing with the Ektachem 700 analyzer. The % CVs were calculated from the resulting data and are reported in the following Table II.

TABLE II

Precision of Lipophilic Hemispherand Ionophores

| Hemispherand (Structure II) | % CV in Cartridge | | | | |
|---|---|---|---|---|---|
|  | 1 | 5 | 10 | 15 | 20 |
| Benzyl (Control) | 1.7 | 1.9 | 1.3 | 1.3 | 1.2 |
| 2-Decyl | 0.48 | 0.51 | 0.55 | 0.54 | 0.45 |
| 4-t-Butylbenzyl | 0.49 | 0.58 | 0.46 | 0.49 | 0.81 |
| 2-Octyl | 0.51 | 0.54 | 0.80 | NA | NA |
| 3-Octyl | 0.39 | 0.50 | 0.30 | 0.48 | 0.43 |
| Cyclohexylmethyl | 0.60 | 0.96 | 0.91 | 0.89 | NA |

These data show that the lipophilic hemispherands of this invention exhibit greater precision than the 2'-benzyloxy compound of Examples 1 and 2 of U.S. Pat. No. 4,476,007. It should be noted that a precision less than 1.0 is acceptable.

EXAMPLE 8

Other ion-selective electrode slides were used to evaluate the selectivity of the hemispherand ionophores of this invention to Na+ over K+ by spiking the human serum to a concentration of 120 mM with K+ and 140 mM with Na+ before spotting on the slides. The Na+ concentrations were again determined in the Ektachem 700 analyzer, and the differences between the results and the real value of 140 mM (ΔmM) were determined and recorded in Table III.

TABLE III

Selectivity of Lipophilic Hemispherand Ionophores

| Hemispherand (Structure II) | Benzyl (Control) | 2-Decyl | 4-t-Butylbenzyl |
|---|---|---|---|
| ΔmM (120 mM K+ spike) | −7.9 | −6.7 | −9.0 |

The differences ranging from −6.7 to −9.0 are within experimental error and are indicative of very good selectivity for all three ionophores. A combination of ionic strength efforts and liquid junction potential causes these values to be negative if the selectivity of the electrode for sodium over potassium is 100:1 or better. Thus the sodium ion-selective compostions of the present invention retain the high sodium selectivity of the control prior art compostions while substantially improving assay precision for sodium.

The invention has been described in detail with particular reference to preferred embodiments thereof, but it will be understood that variations and modifications can be effected within the spirit and scope of the invention.

We claim:

1. A lipophilic hemispherand compound represented by the structure:

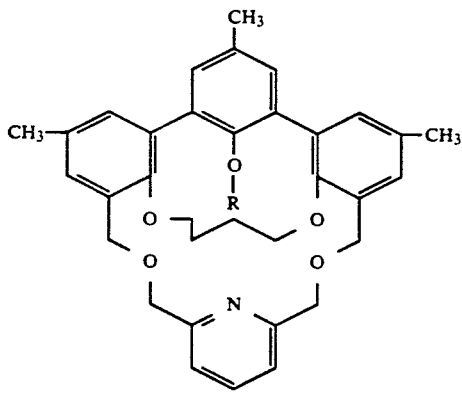

wherein R represents 2-decyl, 2-octyl; 3-octyl and cyclohexylmethyl.

2. A sodium ion-selective composition comprising a solvating compound and a lipophilic hemispherand compound represented by the structure:

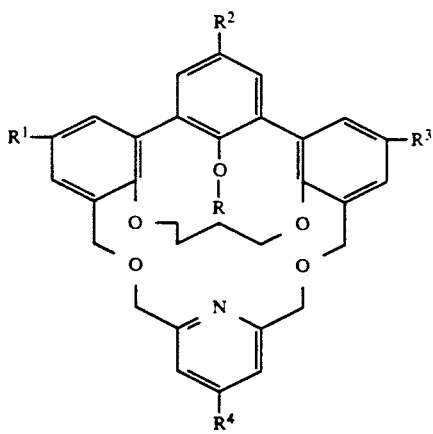

wherein R represents 2-decyl, 2-octyl; 3-octyl and cyclohexylmethyl.

3. The composition of claim 2 comprising a supporting matrix.

4. The composition of claim 2 wherein said solvating compound is a hydrophobic carrier solvent.

5. The composition of claim 4 wherein said carrier solvent is selected from the group consisting of phthalates, sebacates, aromatic and aliphatic ethers, phosphates, mixed aromatic-aliphatic phosphonates, adipates, nitrated ethers or esters, and mixtures thereof.

6. A sodium ion-selective electrode having an ion selective membrane composition comprising an ionophore which is a lipophilic hemispherand compound according to claim 2.

7. A sodium ion-selective electrode comprising:
   (a) a reference electrode in contact with
   (b) a reference composition which is, in turn, in contact with one side of
   (c) an ion-selective membrane composition comprising a solvating compound and a lipophilic hemispherand represented by a structure according to claim 2.

8. The electrode of claim 7 wherein said solvating compound is selected from the group consisting of phthalates, sebacates, aromatic and aliphatic ethers, phosphates, mixed aromatic-aliphatic phosphonates, adipates, nitrated ethers or esters, and mixtures thereof.

9. The electrode of claim 7 wherein said membrane is porous glass.

10. The electrode of claim 7 wherein said membrane is a hydrophobic polymer.

11. A dry-operative sodium ion-selective electrode comprising a lipopholic hemispherand ionophore dissolved in a compound capable of solvating said hemispherand compound, wherein the hemispherand compound has a structure according to claim 2.

12. The electrode of claim 11 wherein said ionophore and solvating compound are distributed within a hydrophobic binder.

13. A dry-operative sodium ion-selective electrode comprising:
   (a) a dried internal reference element comprising the dried residue of a solution of a salt and a hydrophilic polymeric binder in a solvent for the polymer and the salt and,
   (b) in contact with said reference element, a hydrophobic ion-selective membrane of predetermined uniform thickness in regions thereof intended for contact with a sample for analysis, the membrane comprising a hydrophobic polymeric binder having distributed therein a hemispherand compound having a structure according to claim 2 dissolved in a carrier solvent.

14. The electrode of claim 13, wherein said carrier solvent is selected from the group consisting of phthalates, sebacates, aromatic and aliphatic ethers, phosphates, mixed aromatic-aliphatic phosphonates, adipates, nitrated ethers and esters, and mixtures thereof.

* * * * *

UNITED STATES PATENT AND TRADEMARK OFFICE
CERTIFICATE OF CORRECTION

PATENT NO. : 5,132,001
DATED : July 21, 1992
INVENTOR(S) : Vincent Bakos, et al

It is certified that error appears in the above-indentified patent and that said Letters Patent is hereby corrected as shown below:

Column 4, line 9 should read: --A hemispherand is a macrocyclic compound wherein--.

Column 8, line 26: Formula should be relocated to top of column 8.

Column 10, line 8 should read: --3-2'-(-Octyloxy)-3,3"-(2,6-pyridylenebis-(methyleneox---.

Column 10, line 12 should read: --a total of 1.6 equivalent 1-bromooctane and TMG in--.

Column 11, line 34 should read: --Alkylation of Hemispherand Center Phenol--.

Column 12, line 68 should read: --better. Thus the sodium ion-selective compositions of--.

Column 13, line 2 should read: --of the control prior art compositions while substantially--.

Signed and Sealed this

Twenty-sixth Day of October, 1993

Attest:

BRUCE LEHMAN

Attesting Officer     Commissioner of Patents and Trademarks